US005705380A

United States Patent [19]
North et al.

[11] Patent Number: 5,705,380
[45] Date of Patent: Jan. 6, 1998

[54] IDENTIFICATION OF A GENE ENCODING TULP2, A RETINA SPECIFIC PROTEIN

[75] Inventors: Michael North, San Diego, Calif.; Patsy Nishina; Juergen Naggert, both of Bar Harbor, Me.

[73] Assignees: Sequana Theraputics, Inc., La Jolla, Calif.; Jackson Lab., Bar Harbor, Me.

[21] Appl. No.: 706,292

[22] Filed: Sep. 4, 1996

[51] Int. Cl.$^6$ .................. C07H 21/04; C12N 15/63; C12N 15/85

[52] U.S. Cl. .................. 435/240.2; 435/6; 435/91.2; 435/320.1; 536/23.1; 536/235; 536/24.3; 536/24.31; 536/24.33; 935/6; 935/8; 935/77; 935/78

[58] Field of Search ................. 435/6, 91, 91.2, 435/8, 77, 78, 320.1, 240.2; 536/22.1, 23.1, 24.3, 24.33, 24.31, 23.5

[56] References Cited

PUBLICATIONS

5 '→3 ' Catalog (1993) p. 52.
Ausubel et.al., ed.s. Short Protocols in Molecular Biology (1989) pp. 26–28 & 195–196.
Vambutas et al. Biochim. Biophys. Acta 1217:203–206 (Mar. 1994).
Zhang et al. (1995) "Genetic and Molecular Studies of Macular Dystrophies: Recent Developments", *Surv. Ophthalmology* 40:51–61.
Bird (1995) "Retinal Photoreceptor Dystrophies Ll. Edward Jackson Memorial Lecture"*Am. J. Ophthal.* 119:543–562.
Adler (1996) "Mechanisms of Photoreceptor Death in Retinal Degenerations"*Arch. Ophthal.* 114:79–83.
Evans et al. (1994) "Genetic Linkage of Cone–rod Retinal Dystrophy to Chromosome 19q and Evidence for Segregation Distortion"*Nature Genetics* 6:210–213.
Coleman and Eicher (1990) "Fat (Fat) and Tubby (Tub): Two Autosomal Recessive Mutations Causing Obesity Syndromes in the Mouse"*J. Hered.* 81:424–427.
Ohlemiller et al. (1995) "Cochlear and Retinal Degeneration in the tubby Mouse"*Neuroreport* 6:845–849.
Heckenlively et al. (1995) "Mouse Model for Usher Syndrome: Linkage Suggests Homology to Usher Type I Reported at Human Chromosome 11p15"*P.N.A.S.* 92:11100–11104.
Noben–Trauth et al. (1996) "A Candidate Gene for the Mouse Mutation Tubby "*Nature* 380:534–538.
Kleyn et al. (1996) "Identification and Characterization of the Mouse Obesity Gene tubby : A Member of a Novel Gene Family"*Cell* 65:281–290.
Bennett et al. (1996) "Photoreceptor Cell Rescue in Retinal Degeneration (rd) Mice by en vivo Gene Therapy"*Nature Medicine* 2:649–654.
Englehardt et al. (1993) "Direct Gene Transfer of Human CFTR into Human Bronchial Epithelia of Xenografts with E1–deleted Adenoviruses"*Nature Genetics* 4:27–34.
Wang and Finer (1996) "Second–generation Adenovirus Vectors"*Nature Genetics* 2:714.

*Primary Examiner*—W. Gary Jones
*Assistant Examiner*—Debra Shoemaker
*Attorney, Agent, or Firm*—Pamela Sherwood, Ph. D.; Bozicevic & Reed, LLP.

[57] ABSTRACT

The gene responsible for an autosomal dominant con-rod retinal dystrophy is identified, TULP2. The genes are used to produce the encoded protein; in screening for compositions that modulate the expression or function of TULP2 protein; and in studying associated physiological pathways.

6 Claims, No Drawings

IDENTIFICATION OF A GENE ENCODING TULP2, A RETINA SPECIFIC PROTEIN

TECHNICAL FIELD

The field of this invention is genes associated with retinal dystrophies.

BACKGROUND

Vision is fundamentally important throughout life. However, the eye can be a fragile organ, and is susceptible to a number of hereditary and/or age related degenerative disorders. In the United States, a common cause of irreversible blindness or severe loss of vision is retinal dystrophies. The retina is the sensory tunic of the eye, containing light sensitive receptors, a complex of neurons, and pigmented epithelium, arranged in discrete layers. In humans, the macula is the portion of the retina that lies directly behind the lens. Cones, the photoreceptor cells responsible for central vision, are heavily concentrated in the macula. Central dystrophies, which affect the macula, include Best's disease, age-related macular degeneration, and Stargardt's macular dystrophy. The peripheral retina is composed mainly of rods, which are responsible for side and night vision. Peripheral degenerative retinal diseases include cone rod retinal dystrophy, choroidemia and Bietti's crystalline dystrophy.

Inherited eye disorders are the major cause of childhood blindness in the developed world. As much as 50% of all blindness in the United Kingdom has been classified as genetic. Choroidoretinal dystrophies and degenerations are the most common sub-group, all of which are incurable and untreatable. Cone-rod retinal dystrophy (CRD) is a severe example, characteristically leading to early blindness. A loss of color vision and visual acuity is accompanied by widespread, advancing retinal pigmentation and chorioretinal atrophy of the central and peripheral retina. Linkage analysis of a large lineage of autosomal dominant CRD has mapped the disease to chromosome 19q, linked to the polymorphic marker D19S47.

It has been suggested that the disease locus for CRD, which affects central as well as peripheral retina, may also be involved in age-related macular degeneration (ARMD). ARMD affects an estimated 20% of persons over 75 years of age. However, ARMD is poorly understood in terms of etiology and pathogenesis. The very late onset of the disease has made genetic mapping particularly difficult.

It has been previously shown that the mouse mutation, tubby, leads to early progressive retinal and cochlear degeneration, as well as late-onset obesity, insulin resistance and impaired glucose tolerance. Identification by positional cloning revealed tubby to be a novel gene, which is a member of a gene family with a highly conserved carboxy-terminus and variable amino terminus. The prevalence and clinical consequences of retinal dystrophies make it of interest to determine whether other members of this gene family may be associated with retinal disease.

Relevant Literature

Overviews of photoreceptor dystrophies may be found in Cotlier et al. (1995) *Surv. Ophthalmology* 40: 51–61; Bird (1995) *Am. J. Ophthal.* 119: 543–562; and Adler (1996) *Arch Ophthal.* 114: 79–83. Evans et al. (1994) *Nature Genetics* 6: 210–213 describes the genetic mapping of cone-rod retinal dystrophy.

The mouse tub mutation is described in Coleman and Eicher (1990) *J Hered* 81: 424–7 as an autosomal recessive mutation located on chromosome 7, which causes slowly developing but ultimately severe obesity. Ohlemiller et al. (1995) *Neuroreport* 6: 845–9 and Heckenlively et al. (1995) *P.N.A.S.* 92: 11100–11104 describe hearing loss and progressive retinal degeneration in tubby mice. The retinal degeneration is characterized by loss of photoreceptor cells, resulting in abnormal electroencephalograms by 3 weeks of age. Noben-Trauth et al. (1996) *Nature* 380: 534–538 and Kleyn et al. (1996) *Cell* 65: 281–290 describe the human and mouse genes associated with tubby. The carboxy terminal 260 amino acids of tubby show a strong similarity to a mouse testis-specific cDNA (GenBank accession number X69827).

Bennett et al. (1996) *Nature Medicine* 2: 649 demonstrate that injection into rd/rd mice of a recombinant replication defective adenovirus that contains wild-type cDNA encoding βPDE delays photoreceptor death. Adenovirus vectors are described in Englehardt et al. (1993) *Nature Genetics* 4: 27–34, and in Wang and Finer (1996) *Nature Medicine* 2: 714.

SUMMARY OF THE INVENTION

Nucleic acid compositions are provided that encode a mammalian retina-specific protein, TULP2. The human TULP2 locus is associated with a genetic predisposition to cone-rod retinal dystrophy. The nucleic acid compositions find use in identifying DNA sequences encoding homologous or related proteins; for production of the encoded protein; and in studying associated physiological pathways. In addition, modulation of the gene activity in vivo is used for prophylactic and therapeutic purposes, such as treatment of retinal degeneration, identification of retinal cells based on expression, and the like. The DNA is further used as a diagnostic for genetic predisposition to cone rod retinal degeneration.

BRIEF DESCRIPTION OF THE SEQUENCES

The complete cDNA sequence of human TULP2 is provided in SEQ ID NO:1, and its predicted amino acid sequence in SEQ ID NO:2.

DESCRIPTION OF THE SPECIFIC EMBODIMENTS

Mammalian genes associated with retinal degeneration are provided (TULP2). Of particular interest are the human gene sequences. The TULP2 locus is associated with a predisposition to cone-rod retinal dystrophy (CRD). TULP2 nucleic acids are used to identify homologous or related genes, to identify retinal and testis cells based on gene expression, to produce the corresponding protein, and as a diagnostic for a specific genetic predisposition to blindness affecting the central and peripheral retina. The encoded protein is useful as an immunogen to raise antibodies that specifically identify retinal and testis cells, in drug screening assays directed at retinal degeneration, and for therapeutic purposes.

The tubby gene family is a group of related genes characterized by a highly conserved carboxy terminus and variable amino terminus. While tubby is expressed in a number of different cell types, the expression of TULP2 is restricted to the retina and testes. Retinal expression in adult tissue is relatively low. It will be understood by one of skill in the art that low basal levels of transcription may be present in other normal cell types, or that a relatively rare cell type may have a high level of expression that cannot readily be detected in mRNA prepared from whole tissue.

By specific expression, it is intended that mRNA levels are increased above the basal levels observed in non-retinal cells by at least about 100 fold. It will be further understood that malignant, or transformed, cells may express genes in an aberrant fashion.

Nucleic acids encoding TULP2 may be cDNA, mRNA or genomic DNA, or a fragment thereof. The term "gene" shall be intended to mean an open reading frame encoding a specific TULP2 polypeptide, as well as adjacent 5' and 3' non-coding nucleotide sequences involved in the regulation of expression, up to about 1 kb beyond the coding region, in either direction. The gene may be introduced into an appropriate vector for extrachromosomal maintenance or for integration into the host.

The term "cDNA" as used herein is intended to include all nucleic acids that share the arrangement of sequence elements found in native mature mRNA species, where sequence elements are exons, 3' and 5' non-coding regions. Normally mRNA species have contiguous exons, with the intervening introns deleted, to create a continuous open reading frame.

Genomic TULP2 sequences have non-contiguous open reading frames, where introns interrupt the coding regions. A genomic sequence of interest comprises the nucleic acid present between an initiation codon and stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb of flanking genomic DNA at either the 5' or 3' end of the coding region. The genomic DNA may be isolated as a fragment of 50 kbp or smaller. A preferred genomic sequence will lack those sequences that are linked to TULP2 in a native chromosome but which do not contribute to the biological function of the TULP2 gene.

The nucleic acid compositions of the subject invention encode all or a part of the subject polypeptides. Fragments may be obtained of the DNA sequence by chemically synthesizing oligonucleotides in accordance with conventional methods, by restriction enzyme digestion, by PCR amplification, etc. For the most part, DNA fragments will be of at least 25 nt, usually at least 30 nt, more usually at least about 50 nt. Such small DNA fragments are useful as primers for PCR, hybridization screening, etc. Larger DNA fragments, i.e. greater than 100 nt are useful for production of fragments of the encoded polypeptide.

Where it is desirable to generate probes or primers that distinguish TULP2 from other members of the human TUBBY gene family, sequences may be derived from the less conserved region of the gene, which includes nucleotides 0 through 1050 of SEQ ID NO:1; particularly nt. 0–150 and 900–1050. Probes that will broadly recognize members of the TUBBY gene family may be derived from the conserved region of the gene, which includes nucleotides 1050 through 1700, particularly nt. 1430–1650.

For use in amplification reactions, such as PCR, a pair of primers will be used. The exact composition of the primer sequences is not critical to the invention, but for most applications the primers will hybridize to the subject sequence under stringent conditions, as known in the art. It is preferable to chose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The DNA sequences are obtained in substantial purity, generally as a sequence other than a sequence of an intact mammalian chromosome. Usually, the DNA will be obtained substantially free of other nucleic acid sequences that do not include a TULP2 sequence or fragment thereof, generally being at least about 50%, usually at least about 90% pure and are typically "recombinant", i.e. flanked by one or more nucleotides with which it is not normally associated on a naturally occurring chromosome.

The DNA sequences may be used in a variety of ways. They may be used as probes for identifying other TULP polypeptides, including novel subfamily members, homologs and syntenic homologs. Mammalian homologs have substantial sequence similarity to the subject sequences, i.e. at least 80%, preferably at least 90%, more preferably at least 95% sequence identity with the nucleotide sequence of the subject DNA sequence. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithims for sequence analysis are known in the art, such as BLAST, described in Altschul et al. (1990) *J Mol Biol* 215: 403–10.

Non-identical nucleic acids with sequence similarity are detected by hybridization under low stringency conditions, for example, at 50° C. and 10XSSC (0.9M saline/0.09M sodium citrate) and remain bound when subjected to washing at 55° C. in 1XSSC. By using probes, particularly labeled probes of DNA sequences, one can isolate homologous or related genes. The source of homologous genes may be any mammalian species, e.g. primate species, particularly human; murines, such as rats and mice, canines, felines, bovines, ovines, equines, etc.

For hybridization probes, it may be desirable to use nucleic acid analogs, in order to improve the stability and and binding affinity. A number of modifications have been described that alter the chemistry of the phosphodiester backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire phosphodiester backbone with a peptide linkage.

Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

The DNA sequences, particularly nucleic acid analogs as described above, may be used as antisense sequences. The antisense sequences may be used by themselves or in conjunction with various toxic moieties, such as metal chelates, sensitizers, ribozymes, and the like. Antisense sequences may be used to study the effect of TULP2 loss of function.

Nucleic acid probes may also be used to identify expression of the gene in a biological specimen, e.g. retinal or testis cells. The manner in which one probes cells for the presence of particular nucleotide sequences, as genomic DNA or RNA, is well-established in the literature and does not require elaboration here. A biological specimen is used as a source of mRNA. The mRNA may be amplified by RT-PCR, using reverse transcriptase to form a complementary DNA strand, followed by polymerase chain reaction amplification using primers specific for the subject DNA sequences. Alternatively, the mRNA sample is fractionated by gel electrophoresis, transferred to a suitable support, e.g. nitrocellulose and then probed with a fragment of the subject DNA as a probe. Other techniques may also find use. Detection of mRNA having the subject sequence is indicative of TULP2 gene expression in the sample.

The TULP2 genes and fragments thereof, encoded protein, and anti-TULP2 antibodies are useful in the identification of individuals predisposed to retinal dystrophies. Of particular interest are diseases that affect the central and peripheral retina, such as CRD. The characterization is useful in determining further treatment of the patient. DNA from a patient having a retinal dystrophy, e.g. CRD, associated with a TULP2 gene is analyzed for the presence of a predisposing mutation in the gene. The presence of a mutated TULP2 sequence that affects the activity or expression of the encoded gene product confers an increased susceptibility to this condition. Specific mutations of interest include any mutation that leads to retinal degeneration, including insertions, substitutions and deletions in the coding region sequence, introns that affect splicing, promoter or enhancer that affect the activity and expression of the protein. A "normal" cDNA sequence of human TULP2 is provided in SEQ ID NO:1. The normal TULP2 sequence shall be understood to include sequence variants in non-coding regions that do not affect the level of expression of the gene, coding region variants that do not change the amino acid sequence, e.g. "third position" changes, and changes that result in an altered amino acid sequence but maintain substantially all of the normal protein function.

Biochemical studies may be performed to determine whether a candidate mutation in the TULP2 coding region or control regions predisposes to disease. For example, the activity of a candidate TULP2 protein may be compared with the wild-type protein activity. A change in the promoter or enhancer sequence that downregulates expression of TULP2 may also result in predisposition to retinal degeneration. Expression levels of a candidate variant allele are compared to expression levels of the normal allele by various methods known in the art. Methods for determining promoter or enhancer strength include quantitation of the expressed natural protein; insertion of the variant control element into a vector with a reporter gene such as β-galactosidase, chloramphenical acetyltransferase, etc. that provides for convenient quantitation; and the like.

Retinal dystrophies of interest also include age related macular dystrophy, Stargardt's macular dystrophy, Best's disease, pigment pattern dystrophies, central alveolar choroidal dystrophy, dominant drusen, hereditary hemorrhagic macular dystrophy, North Carolina macular dystrophy, peri-central choroidal dystrophy, adult foveomacular dystrophy, benign concentric annular macular dystrophy, central aureolar pigment epithelial dystrophy, congenital macular coloboma, dominantly inherited cystoid macular edema, familial foveal retinoschisis, fenestrated sheen macular dystrophy, progressive foveal dystrophy, slowly progressive macular dystrophy, Sorsby's pseudoinflammatory dystrophy, progressive cone dystrophy, Leber's congenital amaurosis and Goldman-Favre syndrome.

A number of methods are used to determine the presence of a predisposing mutation in an individual. Genomic DNA is isolated from the individual or individuals that are to be tested, from any nucleated cellular source, such as blood, hair shafts, saliva, mucous, biopsy material, feces, etc. Where large amounts of DNA are available, the genomic DNA may be used directly. Alternatively, the region of interest is cloned into a suitable vector and grown in sufficient quantity for analysis, or amplified by conventional techniques.

Methods using PCR amplification can be performed on the DNA from a single cell, although it is convenient to use at least about $10^5$ cells. A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high afifnity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The amplified or cloned fragment may be sequenced by dideoxy or other methods, and the sequence of bases compared to the normal TULP2 sequence. Various methods are known in the art that utilize oligonucleotide ligation as a means of detecting mutations, see Riley et al. (1990) *N. A. R.* 18: 2887–2890; and Delahunty et al. (1996) *Am. J. Hum. Genet.* 58: 1239–1246. Alternatively, where the predisposing mutation creates or destroys a recognition site for a restriction endonuclease, the fragment is digested with that endonuclease, and the products size fractionated to determine whether the fragment was digested. Fractionation is performed by gel electrophoresis, particularly acrylamide or agarose gels. Hybridization with the variant sequence may also be used to determine its presence, by Southern blots, dot blots, etc. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. The hybridization pattern of a control and variant sequence to an array of oligonucleotide probes immobilised on a solid support, as described in WO 95/11995, may also be used as a means of detecting the presence of variant sequences.

The subject nucleic acids can be used to generate transgenic animals or site specific gene modifications in cell lines. The modified cells or animals are useful in the study of TULP2 function and regulation. For example, a series of small deletions or substitutions may be made in the TULP2 gene to determine the role of different coding regions in retinal degeneration, signal transduction, substrate binding, etc.

DNA constructs for homologous recombination will comprise at least a portion of the TULP2 gene with the desired genetic modification, and will include regions of homology to the target locus. Conveniently, markers for positive and negative selection are included. Methods for generating cells having targeted gene modifications through homologous recombination are known in the art. For various techniques for transfecting mammalian cells, see Keown et al. (1990) *Methods in Enzymology* 185: 527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination. Those colonies that show homologous recombination may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimetic progeny can be readily detected. The chimeric animals are screened for the presence of the modified TULP2 gene and males and females having the modification are mated to produce homozygous progeny. The transgenic animals may be used to determine the effect of a candidate drug on retinal degeneration in an in vivo environment.

Investigation of gene function may also utilize non-mammalian models, particularly using those organisms that are biologically and genetically well-characterized, such as *C. elegans, D. melanogaster* and *S. cerevisiae*. The subject gene sequences may be used to complement defined genetic lesions in order to determine the physiological and biochemical pathways involved in TULP2 function. A number of human genes have been shown to complement mutations in lower eukaryotes. Drug screening may be performed in combination with complementation studies. Many mammalian genes have homologs in yeast and lower animals. The study of such homologs' physiological role and interactions with other proteins can facilitate understanding of biological function. In addition to model systems based on genetic complementation, yeast has been shown to be a powerful tool for studying protein-protein interactions through the two hybrid system described in Chien et al. (1991) *P.N.A.S.* 88: 9578–9582.

To produce TULP2 proteins the encoding nucleic acid sequences are expressed by insertion into an appropriate expression vector, where the native transcriptional initiation region may be employed or an exogenous transcriptional initiation region, i.e. a promoter other than the promoter which is associated with the gene in the normally occurring chromosome. The promoter is operably linked to the coding sequence of a TULP2 gene to produce a translatable mRNA transcript. The promoter may be introduced by recombinant methods in vitro, or as the result of homologous integration of the sequence into a chromosome. A wide variety of constitutive or inducible promoters are known for a wide variety of expression hosts, where the expression hosts may be prokaryotes or eukaryotes, particularly *E. coil; B. subtills;* yeast cells; mammalian cells; e.g. Cos cells, HeLa cells, L(tk-), primary cultures; insect cells; Xenopus laevis oocytes; and the like. Many strong promoters for mammalian cells are known in the art, including the β-actin promoter, SV40 early and late promoters, immunoglobulin promoter, human cytomegalovirus promoter, retroviral LTRs, etc.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e., increased protein synthesis, stability, reactivity with defined antisera, an enzyme marker, e.g. β-galactosidase, etc.

Expression cassettes may be prepared comprising a transcription initiation region, the TULP2 gene or fragment thereof, and a transcriptional termination region. Of particular interest is the use of sequences that allow for the expression of functional epitopes or domains, usually at least about 24 nucleotides in length, more usually at least about 48 nucleotides in length, and up to the complete open reading frame of the gene. After introduction of the DNA, the cells containing the construct may be selected by means of a selectable marker, the cells expanded and then used for expression.

The expression cassettes may be introduced into a variety of vectors, e.g. plasmid, BAC, YAC, bacteriophage such as lambda, P1, M13, etc., animal or plant viruses, and the like, where the vectors are normally characterized by the ability to provide selection of cells comprising the expression vectors. The vectors may provide for extrachromosomal maintenance, particularly as plasmids or viruses, or for integration into the host chromosome. Where extrachromosomal maintenance is desired, an origin sequence is provided for the replication of the plasmid, which may be low- or high-copy copy number. A wide variety of markers are available for selection, particularly those which protect against toxins, more particularly against antibiotics. The particular marker that is chosen is selected in accordance with the nature of the host, where in some cases, complementation may be employed with auxotrophic hosts. Introduction of the DNA construct may use any convenient method, e.g. conjugation, bacterial transformation, calcium-precipitated DNA, electropotation, fusion, transfection infection with viral vectors, biolistics, etc.

The DNA sequence may encode amino acid sequences that differ from the native sequence of a TULP2 polypeptide. The sequence may encode polypeptide analogs, fragments or derivatives of substantially similar polypeptides that differ from the naturally-occurring forms in terms of the identity of location of one or more amino acid residues (deletion analogs containing less than all of the residues specified for the protein, substitution analogs wherein one or more residues are replaced by other residues and addition analogs wherein one or more amino acid residues are added to a terminal or medial portion of the polypeptides) and which share some or all of the properties of naturally-occurring forms. Of particular interest are mutations that confer a genetic predisposition to retinal degeneration.

Sequence analogs include the incorporation of preferred codons for expression in non-mammalian host cells; the provision of sites for cleavage by restriction endonuclease:enzymes; the addition of promoters operatively linked to enhance RNA transcription and the provision of additional initial, terminal or intermediate DNA sequences that facilitate vector construction.

With the availability of the protein in large amounts by employing an expression host, the protein may be isolated and purified in accordance with conventional ways. A lysate may be prepared from the expression host and purified using HPLC, exclusion chromatography, gel electrophoresis, affinity chromatography, or other purification techniques as known in the art. The purified protein will generally be at least about 80% pure, preferably at least about 90% pure, and may be up to 100% pure. By pure is intended free of other proteins, as well as cellular debris.

Polypeptides may be used for the production of antibodies. Antibodies are prepared in accordance with conventional methods, where the expressed polypeptide or protein is used as an immunogen, by itself or conjugated to known immunogenic carriers, e.g. KLH, BSA, etc. Various adjuvants may be employed, as appropriate. For monoclonal antibodies, after one or more booster injections, the spleen of the immunized animal is isolated, the splenocytes immortalized and then screened for high affinity antibody binding. The immortalized cells, i.e. hybridomas, producing the desired antibodies may then be expanded. For further description, see *Monoclonal Antibodies: A Laboratory Manual*, Harlow and Lane eds., Cold Spring Harbor Laboratories, Cold Spring Harbor, N.Y., 1988. The antibodies find use in diagnostic assays for detection of the presence of TULP2 in patient samples, and as a means of identifying TULP2-expressing cells.

By providing for the production of large amounts of TULP2 protein, one can identify ligands or substrates that bind to, or modulate the action of TULP2. The purified protein may be used for determination of three-dimensional crystal structure, which can be used for modeling intermolecular interactions. The subject polypeptides or functional domains thereof are used to screen for agonists or antagonists that modulate the interaction of TULP2 with its normal substrate, or proteins with which TULP2 interacts in a normal cell. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like.

The term "agent" as used herein describes any molecule, protein, or pharmaceutical with the capability of mimicking, or directly or indirectly altering the physiological function of TULP2. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like, Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce nonspecific or background interactions. Reagents that improve the efficiency of the assay, such as protease inhibitors, nuclease inhibitors, anti-microbial agents, etc. may be used.

The mixture of components are added in any order that provides for the requisite binding. Incubations are performed at any temperature that facilitates optimal activity, typically between 4° and 40° C. Incubation periods are selected for optimum activity, but may also be optimized to facilitate rapid high-throughput screening. Typically between 0.1 and 1 hours will be sufficient.

The compounds having the desired pharmacological activity may be administered in a physiologically acceptable carrier to a host for treatment of retinal degeneration attributable to a defect in TULP2 function. The inhibitory agents may be administered in a variety of ways, orally, parenterally e.g. subcutaneously, intraperitoneally, intravascularly, etc. Depending upon the manner of introduction, the compounds may be formulated in a variety of ways. The concentration of therapeutically active compound in the formulation may vary from about 0.1-100 wt. %.

The pharmaceutical compositions can be prepared in various forms, such as ocular implants, granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value.

The present data suggest that TLP proteins are associated with degeneration of specific neural cells, e.g. photoreceptors, in the retina. The disease histology is consistent with apoptosis of affected cells. The availability of the subject gene sequences provides a means of analyzing the biology and biochemistry of specific retinal degeneration through in vitro and in vivo drug screening, the use of transgenic animals, complementation of specific genetic lesions, etc., as previously described.

A pathways of particular interest is photoreceptor apoptosis. Mutations in the β subunit of cGMP phosphodiesterase cause retinal degeneration in mice with the rd1 mutation and in humans, and in rd1/rd1 mice an abnormal accumulation of cGMP appears to trigger apoptosis of the photoreceptor cells.

Drug screening assays may be performed with mutant and wild-type TULP2 protein to detect agents that mimic or act as agonists or antagonists for TULP2 function. The interaction of TULP2 with other proteins in these pathways is of particular interest, and may be detected in a variety of assays, e.g. yeast two hybrid system, in vitro protein-protein binding assays, genetic complementation, etc. There are a number of characterized genes and gene products that operate to regulate or effect apoptosis.

Complementation in animal and yeast models is particularly useful in the study of apoptosis. The genetics of programmed cell death has been well-defined in several animal models. Both C. elegans and D. melanogaster regulate apoptosis through the expression of two gene products, ced-3 and ced-9, and rpr and hid, respectively. The relative simplicity of these pathways is attractive for biochemical and genetic analysis. Both animals are used as screening tools in conjunction with the subject gene sequences, and with their corresponding TULP2 homologs.

A number of apoptotic and anti-apoptotic genes are expressed in neurons and photoreceptors, and may be involved in retinal degeneration. These cells depend on factors such as nerve growth factor and brain derived neurotrophic factor for survival, and may undergo apoptosis where the factor or its receptor are mutated. Among the anti-apoptotic genes of interest are bcl-2, bcl-xL and mcl-1. Inducers of apoptosis include fas (CD95), myc, bax, bcl-xs, TNF receptor and the family of cysteine proteases that includes interleukin 1 β-converting enzyme.

The subject TULP2 genes are useful in gene therapy to prevent the photoreceptor death caused by CRD. Of particular interest is intraocular gene delivery, e.g. sub-retinal injection, ocular implants, etc. The therapeutic gene is delivered through a suitable vector. e.g. a plasmid or viral vector. Viral vectors known in the art include modified retroviral genomes such as moloney leukemia virus and human immunodeficiency virus. Retroviral vectors typically include viral sequences that are required for packaging, integration and expression of the inserted TULP2 genes. The vectors are "defective" in the ability to encode viral proteins required for productive infection. Replication requires growth in a packaging cell line that provides the gag, pol, and env proteins necessary for completion of the infectious cycle. Adenovirus vectors are also of interest, as described in Li et al. (1994) Invest. Ophthalmol. Vis. Sci. 35: 2543–2549; and Bennett et al: supra.

The following examples are offered by way of illustration and not by way of limitation.

EXPERIMENTAL

TULP2 was identified as a member of the tubby gene family. TULP2 cDNA was isolated by hybridization of a probe from the mouse p46 sequence, at reduced stringency, to a human cDNA library. The mouse p46 gene was previously identified as a cDNA sequence in a public database, with homology to tubby. TULP2 extends approximately 700 bp further than p46 on its 5' end, and has numerous nucleotide differences throughout the length of the gene. The p46 sequence has the GenBank accession number X69827.

Identification of the Mouse tubby and P46 Genes

Tubby is a mutation arose spontaneously in the C57BL/6J mouse strain. Homozygotes are recognizable by increased body weight at 3 to 4 months in males and at 4 to 6 months in females. The associated gene was identified by genetic mapping, following by physical characterization of the locus.

Genetic Mapping. Tubby was previously mapped in an interspecific (CS1BL/6-tub/tub X CAST/Ei)$F_1$ intercross to 2.4±1.4 cM from Hbb. Three mapping crosses were then used to refine the minimal region containing the gene to between markers D7Mit94 and D7Mit325. DNA samples isolated from the progeny of crosses between C57BL/6-tub/tub, CAST/Ei, AKR or NOD.NON-H2K$^b$ were genotyped for simple sequence length polymorphisms (Dietrich et al. (1994) Nature Genet. 7: 220–245). All recombinants were progeny tested with a minimum of 20 offspring to confirm phenotypic classification. PCR amplification was performed as described in Naggert et al. (1995) Nature Genet. 10: 135–141.

The minimal region containing tub identified by the CAST/El outcrosses was between markers D7Mit124 and D7Mit328 with a genetic distance of 0.27 ±0.14 cM. In the NOD.NON-H2K$^b$ intercross with C57BL/6 tub/tub, the minimal genetic interval containing tub lay between markers D7Mit219 and D7Mit130 with a genetic distance of 0.18±0.11 cM. In the (C57BLI6-tub/tub X AKR)$F_1$ intercross, the genetic interval lay between D7Pjn12 and D7Mit328, corresponding to a distance of 0.19±0.11 cM.

Physical Mapping. A YAC contig was established spanning the minimal genetic region. A high resolution physical map of the region was constructed by P1, BAC and cosmid assembly using STSs derived from end sequencing P1s, by subcloning and sequencing YAC derived cosmid pools, and by searching public databases.

Selected cDNA clones were sequenced and analyzed for similarities to known sequences in GenBank. Unique cDNA clones and single clones from groups of overlapping clones were hybridized to Southern blots of EcoRI digested P1 DNA. Positive clones that mapped to the minimal region were analyzed for genomic alterations and aberrant expression between C57BL/6 and C57BLI6-tub/tub mice. One cDNA clone showed an altered hybridization pattern in tubby derived mRNA when compared to C57BU6, and was identified as the tubby gene. The DNA sequence has the GenBank accession number U52433.

Using the BLASTN program (described in Altshul et al. (1990) J. Mol. Bio. 215: 403–410), the carboxy terminal 260 amino acids of tubby showed a strong similarity (62% identity) to the putative mouse testis-specific cDNA p46 (GenBank accession number X69827).

Isolation of TULP2 cDNA

Approximately $1 \times 10^6$ pfu of human testis cDNA library in lambda DR2. (Clontech) were plated according to the manufacturer's instructions, using K802 as bacterial host.

After over night incubation at 37° C., 2 membranes were lifted from each plate. Those membranes were hybridized in 10% dextran sulfate, 1% SDS, 1M NaCl, 100 ug/ml of salmon testes DNA and $^{32}$P labeled probes at 65° C. for 16 hr.

The labeled probe was a PCR amplification product from a mouse testis cDNA library. Using primers MP46.1 (SEQ ID NO:3) 5'-TCTACAGAGACAAACTATGCCC-3' and MP46.2 (SEQ ID NO:4) 5'-GGAAATGTGCTACACCATC CTC-3', which were designed using the published mouse P46 gene sequence. After hybridization, 3 washes were performed at 55° C.: 2xSSC, 0.1% SDS for 45 min. 0.2xSSC, 0.1% SDS for 45 min, 0.2xSSC, 0.1% SDS for 45 min. 34 positive plaques were detected after overnight exposure with X ray film. 28 positive clones were isolated after tertiary screening. The positive TULP2 clones were converted to plasmid DNA following the manufacturer's protocol and sequenced according to standard protocols.

Human multiple tissue northern blots MTNI, II and III (Clontech) were hybridized with the $^{32}$p labeled PCR amplification product of TULP2, using primers HP46.F1 (SEQ ID NO.:5) 5'-CCACTAAATGAACAGGAGTCGC-3' and HP46.R1 (SEQ ID NO:6) 5'-GAAACTGGACAAGCAGATGCTG-3'. The probe corresponds to nt 1360–1650 of TULP2, (SEQ ID NO:1). The hybridization was done in ExpressHyb solution (Clontech) at 60° C. for 2 hr, according to the manufacturer's instructions. The blots were washed 3 times in 2xSSC, 0.05% SDS at room temp, followed by washing with 0.1xSSC, 0.1%SDS at 55° C. 2×40 min., with 0.1xSSC,0.1% SDS at 65° C. for 40 min. The TULP2 transcript was detected only in testis, with an approximate size of 1.8 kb.

In order to detect retinal expression, a human retinal cDNA library (Clontech) was plated, and filters lifted, as described above. Using the same TULP2 probe and hybridization conditions, positive plaques were identified at a frequency of 1/10$^6$ plaques, indicating low level expression in adult retina tissue.

The genomic location of TULP2 was mapped using the Genebridge radiation hybrid panel. Oligonucleotide primers for PCR amplification were constructed from the 2nd exon from 3' end of TULP2 (position 1360–1521 ), generating a product of 162 bp in both cDNA and genomic DNA. The primers used were:

(SEQ ID NO:7) HP46. F1 5'-CCACTAAATGAACAG-
GAGTCGC-3'

(SEQ ID NO:8) HP46.R2 5'-TTGGAAGTTCTTCACCGAAGCC-
3'

The PCR conditions were 94° C., 45 sec; 55° C., 45 sec; 72° C., 60 sec for a total of 30 cycles. After confirming by sequencing that the appropriate product was amplified, the retention patterns for each oligonucleotide pair were obtained by PCR assay in the Genebridge radiation hybrid panel (see Walter et al. (1994) Nature Genetics 7: 22–28).

Data entered into an online database was analyzed by RHMAP software developed by Boehnke et al. (1991) Am J Hum Genet 49: 1174–1188. The public domain mapping data may be obtained through the Whitehead Institute/MIT Center for Genome Research, Human Genomic Mapping Project, Data Release 10 (May 1996). This data corresponds to the integrated maps announced in Hudson et. al. (1995) Science 270: 1945–1954. Hudson et al. provide a detailed description of the materials and methods used to construct these maps. Further mapping information may be found in Dib et al. (1996) Nature 380: 152–154.

The Genebridge mapping data for TULP2 and WI-9028 is as follows:

WI-9028

0000000001000000001010000000100000000101100110001100000000011110010010
01000000000201110201

TULP2

0000000001000000101010000010010000000010110011000110000000000010110010000
01000000000201110201

These data indicate that the TULP2 gene is most tightly linked (with lod>3) at 3.05 cR to framework marker WI-9028, which maps within the reported linked interval for 19q rod cone retinal dystrophy. The gene for rod cone dystrophy maps between D19S212 and D19S214.

It is evident from the above results that a novel member of the tubby gene family has been characterized. TULP2 is expressed in the testes and retina, but not in other adult tissue. Genomic mapping data indicate that the gene is closely associated with the locus for cone-rod retinal dystrophy, a disease causing early chorioretinal atrophy of the central and peripheral retina.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid molecule or complement thereof consisting of a nucleic acid sequence encoding a human TULP2 protein wherein the protein has the amino acid sequence of SEQ ID NO:2.

2. An isolated nucleic acid molecule according to claim 1, wherein said nucleic acid consists of the nucleotide sequence of SEQ ID NO:1 or complement thereof.

3. An isolated nucleic acid molecule according to claim 1, wherein said nucleic acid molecule further comprises a transcriptional initiation region operably linked to said nucleic acid sequence encoding a human TULP2 protein.

4. A cell comprising a nucleic acid molecule according to claim 3.

5. A hybridization probe consisting of at least 25 contiguous nucleotides of SEQ ID NO: 1 or the complement thereof, wherein said probe specifically hybridizes to SEQ ID NO: 1.

6. A hybridization probe consisting of at least 50 contiguous nucleotide of SEQ ID NO: 1 or the complement thereof, wherein said probe specifically hybridizes to SEQ ID NO: 1.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 1733 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:1:

```
GGAATCCTCC CTCCCTCTGA GCCGTCTTTC TTCTCCTCCC TATTTCGCAG ATATCCCGAG      60
ATTAGGTCCC CAGCTTCCAA AGAGAGGATC AGAATGTCTC AGGATAATGA CACATTGATG     120
AGAGACATCC TGGGGCATGA GCTCGCTGCT ATGAGGCTGC AGAAGCTGGA ACAGCAGCGG     180
CGGCTGTTTG AAAAGAAGCA GCGACAGAAG CGCCAGGAGC TCCTCATGGT TCAGGCCAAT     240
CCTGACGCTT CCCCGTGGCT TTGGCGCTCT TGTCTGCGGG AGGAGCGCCT TTAGGTGAC     300
AGAGGCCTTG GGAACCCTTT CCTCCGGAAG AAAGTGTCAG AGGCACATCT GCCCTCTGGC     360
ATCCACAGTG CCCTGGGCAC CGTGAGCTGT GGTGGAGACG GCAGGGGCGA GCGCGGCCTC     420
CCGACACCGC GGACAGAAGC AGTGTTCAGG AATCTCGGTC TCCAGTCCCC TTTCTTATCC     480
TGGCTCCCAG ACAATTCCGA TGCAGAATTG GAGGAAGTCT CCGTGGAGAA TGGTTCCGTC     540
TCTCCCCCAC CTTTTAAACA GTCTCCGAGA ATCCGACGCA AGGGTTGGCA AGCCCACCAA     600
CGACCTGGGA CCCGTGCAGA GGGTGAGAGT GACTCCCAGG ATATGGGAGA TGCACACAAG     660
TCACCCAATA TGGGACCAAA CCCTGGAATG GATGGTGACT GTGTATATGA AAACTTGGCC     720
TTCCAAAAGG AAGAAGACTT GGAAAAGAAG AGAGAGGCCT CTGAGTCTAC AGGGACGAAC     780
TCCTCAGCAG CACACAACGA AGAGTTGTCC AAGGCCCTGA AGGCGAGGG TGGCACGGAC     840
AGCGACCATA TGAGGCACGA AGCCTCCTTG GCAATCCGCT CCCCCTGCCC TGGGCTGGAG     900
GAGGACATGG AAGCCTACGT GCTGCGGCCA GCGCTCCCGG GCACCATGAT GCAGTGCTAC     960
CTCACCCGTG ACAAGCACGG CGTGGACAAG GGCTTGTTCC CCCTCTACTA CCTCTACCTG    1020
GAGACCTCTG ACAGCCTGCA GCGCTTCCTC CTGGCTGGGC GAAAGAGAAG AAGGAGCAAA    1080
ACTTCTAATT ACCTCATCTC CCTGGATCCT ACACTCCTAT CTCGGGACGG GGACAATTTC    1140
GTGGGCAAAG TCAGATCCAA TGTCTTCAGC ACCAAGTTCA CCATCTTTGA CAATGGGGTG    1200
AATCCTGACC GGGAGCATTT AACCAGGAAT ACTGCCCGGA TCAGACAGGA GCTGGGGGCT    1260
GTGTGTTATG AGCCCAACGT CTTAGGATAC CTGGGGCCTC GGAAAATGAC TGTGATTCTC    1320
CCAGGAACCA ACAGCCAGAA CCAGCGAATC AATGTCCAGC CACTAAATGA ACAGGAGTCG    1380
CTACTGAGTC GTTACCAACG TGGGACAAA CAAGGGTTGC TTTTGTTGCA CAACAAAACC    1440
CCGTCGTGGG ACAAGGAGAA CGGTGTCTAC ACGCTCAATT CCATGGTCG AGTCACTCGG    1500
GCTTCGGTGA AGAACTTCCA AATCGTGGAT CCCAAACACC AAGAACATCT GGTGCTCCAG    1560
TTCGGCCGAG TGGGCCAGA CACATTCACC ATGGACTTCT GCTTTCCATT TAGCCCGCTC    1620
CAGGCCTTCA GCATCTGCTT GTCCAGTTTC AATTAGAAGC TGGCTGTTGA ATAACTCAAT    1680
AAAATACCAT ACCCTTGCCA GCAAAAAAAA AAAAAAAAA AAAAAAAAA AAA            1733
```

( 2 ) INFORMATION FOR SEQ ID NO:2:

( i ) SEQUENCE CHARACTERISTICS:
   ( A ) LENGTH: 520 amino acids
   ( B ) TYPE: amino acid
   ( C ) STRANDEDNESS: double
   ( D ) TOPOLOGY: linear ( i i ) MOLECULE TYPE: protein ( x i ) SEQUENCE DESCRIPTION: SEQ ID NO:2:

```
Met Ser Gln Asp Asn Asp Thr Leu Met Arg Asp Ile Leu Gly His Glu
 1               5                  10                  15

Leu Ala Ala Met Arg Leu Gln Lys Leu Glu Gln Gln Arg Arg Leu Phe
             20                  25                  30

Glu Lys Lys Gln Arg Gln Lys Arg Gln Glu Leu Leu Met Val Gln Ala
         35                  40                  45

Asn Pro Asp Ala Ser Pro Trp Leu Trp Arg Ser Cys Leu Arg Glu Glu
     50                  55                  60

Arg Leu Leu Gly Asp Arg Gly Leu Gly Asn Pro Phe Leu Arg Lys Lys
 65                  70                  75                  80

Val Ser Glu Ala His Leu Pro Ser Gly Ile His Ser Ala Leu Gly Thr
                 85                  90                  95

Val Ser Cys Gly Gly Asp Gly Arg Gly Glu Arg Gly Leu Pro Thr Pro
             100                 105                 110

Arg Thr Glu Ala Val Phe Arg Asn Leu Gly Leu Gln Ser Pro Phe Leu
         115                 120                 125

Ser Trp Leu Pro Asp Asn Ser Asp Ala Glu Leu Glu Glu Val Ser Val
     130                 135                 140

Glu Asn Gly Ser Val Ser Pro Pro Phe Lys Gln Ser Pro Arg Ile
145                 150                 155                 160

Arg Arg Lys Gly Trp Gln Ala His Gln Arg Pro Gly Thr Arg Ala Glu
                 165                 170                 175

Gly Glu Ser Asp Ser Gln Asp Met Gly Asp Ala His Lys Ser Pro Asn
             180                 185                 190

Met Gly Pro Asn Pro Gly Met Asp Gly Asp Cys Val Tyr Glu Asn Leu
         195                 200                 205

Ala Phe Gln Lys Glu Glu Asp Leu Glu Lys Lys Arg Glu Ala Ser Glu
     210                 215                 220

Ser Thr Gly Thr Asn Ser Ser Ala Ala His Asn Glu Glu Leu Ser Lys
225                 230                 235                 240

Ala Leu Lys Gly Glu Gly Gly Thr Asp Ser Asp His Met Arg His Glu
                 245                 250                 255

Ala Ser Leu Ala Ile Arg Ser Pro Cys Pro Gly Leu Glu Glu Asp Met
             260                 265                 270

Glu Ala Tyr Val Leu Arg Pro Ala Leu Pro Gly Thr Met Met Gln Cys
         275                 280                 285

Tyr Leu Thr Arg Asp Lys His Gly Val Asp Lys Gly Leu Phe Pro Leu
     290                 295                 300

Tyr Tyr Leu Tyr Leu Glu Thr Ser Asp Ser Leu Gln Arg Phe Leu Leu
305                 310                 315                 320

Ala Gly Arg Lys Arg Arg Arg Ser Lys Thr Ser Asn Tyr Leu Ile Ser
                 325                 330                 335

Leu Asp Pro Thr Leu Leu Ser Arg Asp Gly Asp Asn Phe Val Gly Lys
             340                 345                 350

Val Arg Ser Asn Val Phe Ser Thr Lys Phe Thr Ile Phe Asp Asn Gly
         355                 360                 365
```

| | | | | | | | | | | | | | |
|---|---|---|---|---|---|---|---|---|---|---|---|---|---|
|Val|Asn 370|Pro|Asp|Arg|Glu|His 375|Leu|Thr|Arg|Asn|Thr 380|Ala|Arg|Ile|Arg|
|Gln 385|Glu|Leu|Gly|Ala|Val 390|Cys|Tyr|Glu|Pro|Asn 395|Val|Leu|Gly|Tyr|Leu 400|
|Gly|Pro|Arg|Lys|Met 405|Thr|Val|Ile|Leu|Pro 410|Gly|Thr|Asn|Ser|Gln 415|Asn|
|Gln|Arg|Ile|Asn 420|Val|Gln|Pro|Leu|Asn 425|Glu|Gln|Glu|Ser|Leu 430|Leu|Ser|
|Arg|Tyr|Gln 435|Arg|Gly|Asp|Lys|Gln 440|Gly|Leu|Leu|Leu|Leu 445|His|Asn|Lys|
|Thr|Pro 450|Ser|Trp|Asp|Lys|Glu 455|Asn|Gly|Val|Tyr|Thr 460|Leu|Asn|Phe|His|
|Gly 465|Arg|Val|Thr|Arg|Ala 470|Ser|Val|Lys|Asn|Phe 475|Gln|Ile|Val|Asp|Pro 480|
|Lys|His|Gln|Glu|His 485|Leu|Val|Leu|Gln|Phe 490|Gly|Arg|Val|Gly|Pro 495|Asp|
|Thr|Phe|Thr|Met 500|Asp|Phe|Cys|Phe|Pro 505|Phe|Ser|Pro|Leu|Gln 510|Ala|Phe|
|Ser|Ile|Cys 515|Leu|Ser|Ser|Phe|Asn 520| | | | | | | | |

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="primers"

( x i ) SEQUENCE DESCRIPTION: SEQ ID NO:3:

TCTACAGAGA CAAACTATGC CC        22

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="primers"

( x i ) SEQUENCE DESCRIPTION: SEQ ID NO:4:

GGAAATGTGC TACACCATCC TC        22

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="primers"

( x i ) SEQUENCE DESCRIPTION: SEQ ID NO:5:

CCACTAAATG AACAGGAGTC GC        22

( 2 ) INFORMATION FOR SEQ ID NO:6:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc ="primers"

( x i ) SEQUENCE DESCRIPTION: SEQ ID NO:6:

GAAACTGGAC AAGCAGATGC TG    22

( 2 ) INFORMATION FOR SEQ ID NO:7:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc ="primers"

( x i ) SEQUENCE DESCRIPTION: SEQ ID NO:7:

CCACTAAATG AACAGGAGTC GC    22

( 2 ) INFORMATION FOR SEQ ID NO:8:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc ="primers"

( x i ) SEQUENCE DESCRIPTION: SEQ ID NO:8:

TTGGAAGTTC TTCACCGAAG CC    22